(12) United States Patent
Bajac et al.

(10) Patent No.: US 11,324,937 B2
(45) Date of Patent: *May 10, 2022

(54) MEDICAL CONNECTOR

(71) Applicant: GVS S.P.A., Zola Predosa (IT)

(72) Inventors: Joao Bajac, Sao Caetano do Sul (BR); Carlos Henrique Alvarez, Indaiatuba (BR)

(73) Assignee: GVS S.P.A., Zola Predosa (IT)

( * ) Notice: Subject to any disclaimer, the term of this patent is extended or adjusted under 35 U.S.C. 154(b) by 403 days.

This patent is subject to a terminal disclaimer.

(21) Appl. No.: 16/658,371

(22) Filed: Oct. 21, 2019

(65) Prior Publication Data

US 2020/0046959 A1 Feb. 13, 2020

Related U.S. Application Data

(63) Continuation of application No. 15/737,879, filed as application No. PCT/IB2016/053921 on Jun. 30, 2016, now Pat. No. 10,485,966.

(30) Foreign Application Priority Data

Jul. 2, 2015 (IT) .......................... UB2015A001860

(51) Int. Cl.
  *A61M 39/10* (2006.01)
  *A61M 39/26* (2006.01)
  *A61M 39/24* (2006.01)

(52) U.S. Cl.
  CPC ............ *A61M 39/10* (2013.01); *A61M 39/26* (2013.01); *A61M 2039/1033* (2013.01); *A61M 2039/1072* (2013.01); *A61M 2039/2426* (2013.01)

(58) Field of Classification Search
  CPC ................... A61N 39/10; A61N 39/26; A61M 2039/1072; A61M 2039/1033; A61M 2039/1066; A61M 2039/2426
  See application file for complete search history.

(56) References Cited

U.S. PATENT DOCUMENTS

| | | | | |
|---|---|---|---|---|
| 6,050,978 A | * | 4/2000 | Orr .................. | A61M 39/26 251/149.1 |
| 6,079,432 A | * | 6/2000 | Paradis ............. | A61M 39/26 137/1 |

(Continued)

FOREIGN PATENT DOCUMENTS

| | | |
|---|---|---|
| EP | 2123322 A2 | 11/2009 |
| EP | 2865410 A1 | 4/2015 |

(Continued)

OTHER PUBLICATIONS

International Search Report and Written Opinion dated Jun. 6, 2016 for PCT/IB2016/053921 to GVS S.P.A. filed Jun. 30, 2016.

*Primary Examiner* — Tiffany Legette
(74) *Attorney, Agent, or Firm* — Vorys, Sater, Seymour and Pease LLP

(57) ABSTRACT

A medical connector including a first rigid body capable of being connected to a medical infusion line and having an elongated tubular element in which there is a conduit opening out at opposite extremities, a first extremity of the tubular element being capable of being directly connected to the medical infusion line, the elongated tubular element being capable of being closed off at one of its first open extremities by a second body associated with the first body. The second body is of yielding material and at least partly covers the elongated element and extends beyond the second extremity of that element in such a way as to close off the (Continued)

opening thereof, such second body being overmoulded onto the first body and forming a single piece therewith.

16 Claims, 2 Drawing Sheets

(56) References Cited

U.S. PATENT DOCUMENTS

| | | | |
|---|---|---|---|
| 2008/0093571 A1 | 4/2008 | Desecki | |
| 2008/0103482 A1* | 5/2008 | Fangrow | A61M 39/10 604/523 |
| 2008/0172003 A1 | 7/2008 | Plishka et al. | |
| 2008/0287920 A1 | 11/2008 | Fangrow et al. | |
| 2010/0108681 A1 | 5/2010 | Jepson et al. | |
| 2011/0130717 A1 | 6/2011 | David et al. | |

FOREIGN PATENT DOCUMENTS

| | | | |
|---|---|---|---|
| WO | 2008048777 A2 | 4/2008 | |
| WO | 2009144583 A1 | 12/2009 | |

* cited by examiner

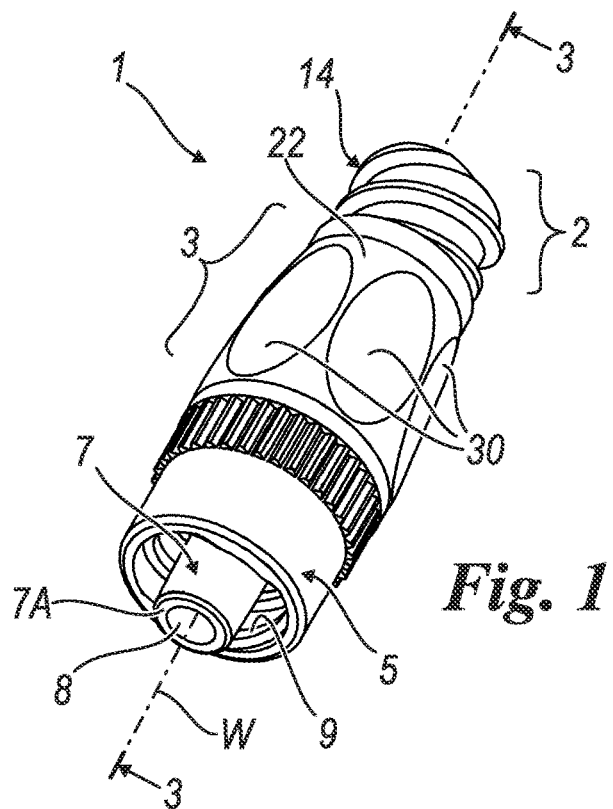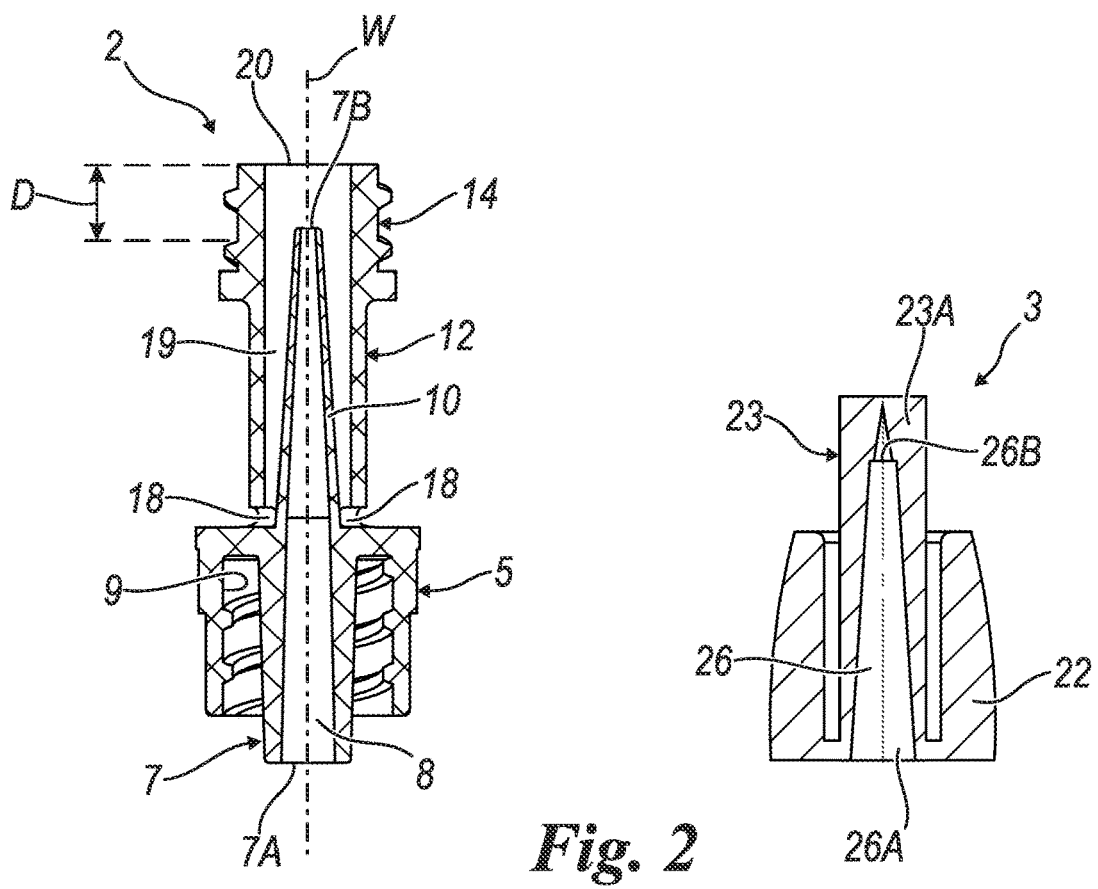

MEDICAL CONNECTOR

CROSS-REFERENCE TO RELATED APPLICATIONS

This application is a continuation of U.S. patent application Ser. No. 15/737,879 filed Dec. 19, 2017, which is a § 371 National Stage Entry of International Application No. PCT/IB2016/053921 filed on Jun. 30, 2016, claiming the priority of Italian Patent Application No. UB2015A001860 filed on Jul. 2, 2015.

This invention relates to a medical connector according to the precharacterising clause of the principal claim.

As is known, in a medical infusion line a tubular member or connector, which is for example "Y"-shaped, through which a drug can be introduced into that line, is frequently provided. For this purpose a plug of yielding material which can be perforated by the needle of a syringe for introducing a drug into the line is placed on one tubular branch of such connector.

This solution therefore provides for the use of a syringe fitted with a needle, something which may also result in contact between it and an operator, with obvious disadvantages. In addition to this the needle may break inside the yielding plug, something which would mean that the entire connector has to be replaced. In addition to this there is also the need to provide for the disposal of used needles, an operation requiring care and attention, which if not performed may result in punctures and corresponding risks for operators involved in disposal.

US 2008/287920 describes a medical connector having the characteristics indicated in the precharacterising part of claim 1. This document describes a medical connector having a first rigid body capable of being connected to a medical infusion line; the rigid body has a tubular portion in which there is a conduit which can be closed off at one extremity by a second body of yielding material which is overmoulded onto the first rigid body. In particular it is described that this second body closes off the extremity of such conduit and is also inserted into the conduit itself. Only a portion of the second body is placed above a corresponding extremity of the tubular portion of the first body.

The yielding body does not enclose such first body and in use, after the medical connector has been detached from the needle of a syringe or a normal Luer connector, such yielding material may come out of the conduit of the tubular portion or even become detached from it. This could expose a medical operator to contact with the medical product present in the connector, a product which could also be toxic to that operator (such as for example a product used in the treatment of cancer).

US 2010/0108681 describes a connection device which can act together with a medical connector without a needle in which such device comprises an axially mobile perforating member.

US 2008/0093571 describes a device activated by a Luer connector comprising a first body having an internal conduit closed off at one extremity by a second body of yielding material capable of acting together with a male Luer connector. This solution has the same disadvantages as described in connection with US 2008/287920 cited above.

WO 2008/048777 describes a medical connector activated by a Luer connector and comprising an elongated body with an internal through conduit which is closed off at one extremity by a resilient element within the medical connector.

This solution also has the disadvantages described for US 2008/287920.

The object of this invention is to provide a medical connector which can receive a fluid from a syringe without the latter having to be provided with a needle.

Another object is to provide an improved medical connector which does not need to be assembled, but which nevertheless comprises two materials, one rigid and one yielding.

Another object is to provide a medical connector of the type mentioned which has low cost and is simple to use.

Another object is to provide a medical connector having a plurality of parts connected together in such a way that they are not able to separate and thus form a single-piece body so as to offer high safety during use to medical operators using it, as well as during emergency actions requiring fast times for connecting the connector to the components of a medical infusion line.

These and other objects which will be obvious to those skilled in the art are accomplished by a medical connector according to the appended claims.

For a better understanding of this invention the following drawings are appended purely by way of example, but without being limiting, in which:

FIG. 1 shows a perspective view of a connector according to the invention from a first angle;

FIG. 2 shows a view in longitudinal cross-section of two components defining the connector in FIG. 1 arranged side by side;

Figure 3:
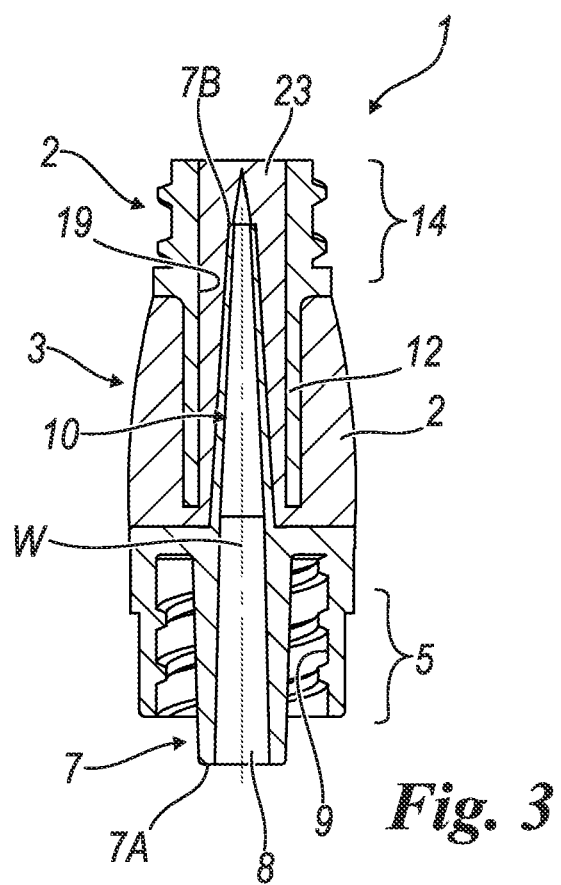
FIG. 3 shows a view in cross-section along the line 3-3 in FIG. 1.
Figure 4:
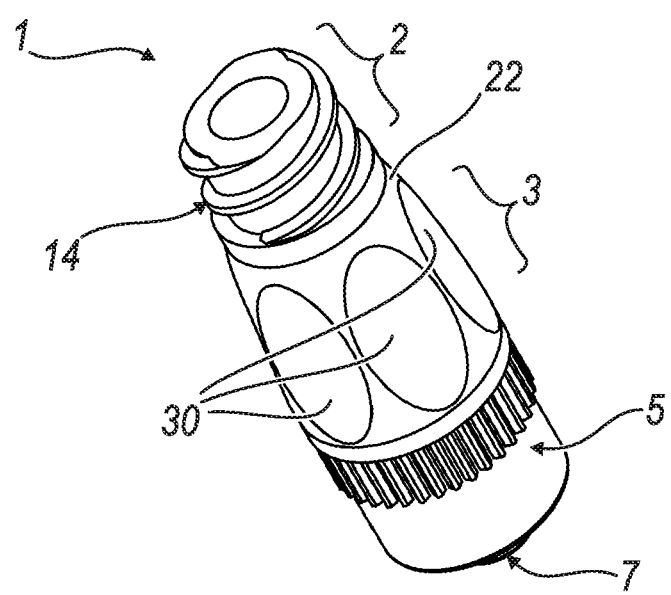
FIG. 4 shows a perspective view of the connector in FIG. 1 from another angle.

With reference to the figures mentioned, a medical connector according to the invention is generically indicated by 1. This comprises two components or main bodies, 2 and 3, which are made of materials having different rigidities; the first component or body 2 is rigid (for example it is of polycarbonate, ABS, PVC and similar rigid materials), while the second 3 is of a yielding material (such as silicone, TPE or the like). This second body or component is overmoulded onto first body 2 and forms a single piece therewith. In FIG. 2 these bodies are shown side by side in order to aid description.

First body 2, which is itself of one piece, has a first extremity portion 5, in the form of a cup and arranged around an inner tubular element 7 having a central conduit 8 located along the axis W of the first body. An inner wall 9 of cup portion 5 is threaded and is able to act together with a normal male Luer connector of a medical line or other medical device having such a connector (not shown).

Through a part 10, tubular element 7 continues within an intermediate portion 12 of first body or component 2 and ends in the second extremity portion 14 of aforesaid body 2. This second extremity portion 14 is externally threaded and is able to act together with a female Luer connector of a syringe without a needle (not shown), which is in itself known.

Part 10 of tubular element 7 is of frustoconical shape. Central conduit 8 of said element 7 opens at extremities 7A and 7B of the latter which respectively correspond to the first and second portions 5 and 14 of body 2. In particular first extremity 7A of element 7 is external to first extremity portion 5 of body 2, while second extremity 7B is internal to abovementioned secondary extremity portion 14.

Between first extremity portion 5 and intermediate portion 12 there is at least one opening and preferably a plurality of openings 18 opening between a space 19 existing around part 10 of tubular element 7 or between this and the wall of the intermediate portion and extremity portions 12 and 14 of body 2. It should be noted that second extremity 7B of the tubular element terminates at a distance D from an opening 20 in second extremity portion 14 of body 2 into which space 19 opens. Through this or such openings the soft material defining the second body is overmoulded onto element 7.

Second body or component 3, whose shape is illustrated individually in FIG. 2, is capable of being overmoulded in space 19 and around intermediate portion 12 of body 2. This second component has a first outer portion 22 which can be placed on the outside of second extremity portion 14 and a second portion 23, attached to first portion 22, capable of being located in space 19 above second extremity 7B of tubular element 7, closing off the opening. This second portion nevertheless remains within second extremity portion 14 of body 2. The connection between first portion 22 and second 23 takes place thanks to the soft and yielding material of second body 3 which penetrates and stops within each opening 18 of body 2. This body 3 is therefore a single component (with its portions 22 and 23) enclosing portion 12.

It should be noted that second portion 23 has an internal cavity 26 opening into its first extremity 26A and closed off at its second extremity 23B. When body 3 is overmoulded onto part 10 of tubular element 7 cavity 26 has a shape matching that of that element.

Internal cavity 26 is instead closed off at its other extremity 26B by a yielding extremity part 23A of second portion 23. This yielding part 23A can split when a syringe without a needle (but having a usual projecting extremity tubular portion) is connected to the second extremity portion 14 of first body or component 2.

It is intended in fact that connector 1 should be connected (as in FIG. 1) to a medical line (not shown) through the first extremity portion 5 of first body 2. In this the syringe without a needle is screwed onto second extremity portion 14 of such body 2. In doing this the normal tubular portion of such syringe "parts" yielding extremity part 23A of second portion 23 and can come into contact with extremity 7B of tubular element 7 connecting to it.

The displaced yielding part seals against the syringe and the tubular element in contact and allows whatever is present in the syringe (for example medical fluid) to be transferred to the latter. When the syringe is separated from connector 1 the resilience of the yielding part seals off tubular element 7.

The solution described therefore relates to a medical connector having two components 2 and 3, the first rigid and the second, of soft and yielding material, being overmoulded onto the first body. This allows for a syringe without a needle to be used to transfer a fluid in a medical line. Safer use by the part of a user of the syringe, for example a nurse, and even safer insertion of that fluid into the medical line is achieved as a consequence.

The connector is also of a single piece and is made in such a way as to close off automatically after being connected to a syringe; in addition to this first portion 22 may be shaped with lowered parts 30 to assist attachment of the connector and its connection to the syringe and/or the medical line.

As a result of the shape in which it is constructed component 3 encloses first component or body 2 and is stably associated therewith, with the impossibility of second body or component 3 becoming detached from the first. This is due to the presence of the connection between portion 22 and 23 of that second body defined by the material of body 3 placed within each opening 18 of body 2.

A preferred embodiment of the invention and its use has been described. Other embodiments and uses are possible, such as that which provides for connector 1 to be associated through second extremity 7B of first body 2 with a branch of a normal X or Y connector, part 7B being nevertheless able to act together with a syringe without a needle to introduce fluids into the X or Y-shaped connector. These variants are also to be understood to fall within the scope of this invention as defined by the appended claims.

The invention claimed is:

1. A method of producing a medical connector comprising a first body capable of being connected to a medical infusion line and having an elongated tubular element comprising: a first extremity portion and a second extremity portion and a conduit opening having a first open extremity that is opposed to a second open extremity, wherein the first open extremity of the elongated tubular element is capable of being directly connected to the medical infusion line, the method comprising overmolding a second body on to the first body to form a single piece between the first body and the second body, the first extremity portion having a first threaded portion for connecting a medical line to the medical connector and the second extremity portion having a second threaded portion to allow the medical connector to be connected to a syringe without a needle or other medical device provided with a female Luer connector, the overmolding of the second body onto the first body such that the second body covers a part of the elongated tubular element and extends beyond the second open extremity to close off the second open extremity, the first body having an intermediate portion between the first threaded portion and the second threaded portion, the part of the elongated tubular element being surrounded by the intermediate portion at a distance from a wall of the intermediate portion to define a space between the wall of the intermediate portion and the part of the elongated tubular element, a second portion of the second body formed to cover the part of the elongated tubular element surrounded by the intermediate portion, the second body further comprising a first portion attached to the second portion of the second body, the second portion formed to extend beyond the intermediate portion of the first body.

2. The method according to claim 1, wherein the first portion of the second body has lowered parts to assist attachment.

3. The method according to claim 1, wherein a material defining the second body connecting the first portion and the second portion of the second body is formed between the first threaded portion and the intermediate portion in at least one opening.

4. The method according to claim 1, wherein the first open extremity is a cup-shaped portion and the first threaded extremity portion is formed on an inner wall of the cup-shaped portion, the first open extremity of the elongated tubular element being formed within the first threaded extremity portion.

5. The method according to claim 1, wherein the second open extremity of the elongated tubular element is formed within the second threaded extremity of the first body, said second portion being formed to overlap the second open extremity of the elongated tubular element.

6. The method of claim 1, further comprising forming the second body from a yielding material.

7. The method of claim 1, further comprising forming the first body from a rigid material.

8. The method of claim 1, wherein the first body is made of a material having different rigidity than the second body.

9. The method of claim 1, wherein the second body is formed of a material that penetrates and stops within a plurality of openings arranged between the first extremity portion and the intermediate portion of the first body.

10. The method of claim 9, wherein the first portion of the second body and the second portion of the second body are connected via the material that penetrates and stops within the plurality of openings arranged between the first extremity portion and the intermediate portion of the first body.

11. The method according to claim 1, wherein the first extremity portion is a cup-shaped portion and the first threaded portion is provided on an inner wall of the cup-shaped portion, the first open extremity formed within the cup-shaped portion, the second open extremity formed within the second threaded portion, the second portion of the second body being formed to overlap the second open extremity.

12. The method according to claim 11, wherein the first open extremity of the elongated tubular element extends from the first threaded portion of the first body.

13. The method according to claim 1, wherein the second portion of the second body is formed to cover the part of the elongated tubular element by being placed in the space between the wall of the intermediate portion and the elongated tubular element.

14. The method according to claim 13, wherein the part of the elongated tubular element is formed to have a frusto-conical shape and includes the second open extremity.

15. The method of claim 1, wherein the second body includes an internal cavity having an open first extremity and a closed second extremity.

16. The method of claim 15, wherein, when the second body is overmolded to the first body, the internal cavity of the second body is of a shape defined by the part of the elongated tubular element.

\* \* \* \* \*